United States Patent [19]

Fruchey

[11] Patent Number: 4,994,613
[45] Date of Patent: Feb. 19, 1991

[54] PROCESS FOR PREPARING 4-HYDROXYACETOPHENONE OXIME WITH MOTHER LIQUOR RECYCLE

[75] Inventor: Olan S. Fruchey, Corpus Christi, Tex.

[73] Assignee: Hoechst Celanses Corporation, Somerville, N.J.

[21] Appl. No.: 470,410

[22] Filed: Jan. 29, 1990

Related U.S. Application Data

[63] Continuation-in-part of Ser. No. 157,186, Feb. 16, 1983, abandoned.

[51] Int. Cl.$^5$ ............................................. C07C 251/44
[52] U.S. Cl. ..................................... 564/259; 564/223
[58] Field of Search ................ 564/259, 223, 300, 383

[56] References Cited

U.S. PATENT DOCUMENTS 2,237,365  4/1941  Schlack ............................... 564/259
3,429,920  2/1969  Rooij .................................... 564/259
3,808,275  4/1974  Hirose et al. ......................... 564/259
4,507,248  3/1985  Mathew et al. ................... 564/259 X
4,524,217  6/1985  Davenport et al. ................. 564/223

OTHER PUBLICATIONS

Shaheen, "Basic Practice of Chemical Engineering", Section 4.3 (1975).

*Primary Examiner*—Richard L. Raymond
*Attorney, Agent, or Firm*—Depaoli & O'Brien

[57] ABSTRACT

A novel process is disclosed for the preparation of 4-hydroxyacetopheone oxime by reaction of 4-hydroxyacetophenone with a hydroxylamine in caustic wherein the mother liquor obtained after crystallization of the oxime together with the wash water is recycled back and reused. This invention illustrates the criticality of maintaining the reactants in certain critical mol ratios in order to obtain 4-hydroxyacetopheone oxime of acceptable color.

4 Claims, No Drawings

PROCESS FOR PREPARING 4-HYDROXYACETOPHENONE OXIME WITH MOTHER LIQUOR RECYCLE

This application is a continuation-in-part, of application Ser. No. 07/157,186, filed Feb. 16, 1988, now abandoned.

BACKGROUND OF THE INVENTION

This invention relates to the production of 4-hydroxyacetophenone (4-HAP) oxime by the conversion of 4-HAP utilizing hydroxylamine. More particularly, this invention is concerned with a process for the production of 4-HAP oxime wherein the mother liquor can be recycled back to the oxime formation step and the color of the 4-HAP oxime which is formed is of good quality. The process of this invention also reduces the amount of mother liquor which is formed because part of it is utilized for recycle, thereby minimizing disposal problems.

In a preferred embodiment, higher concentrations of ammonium sulfate are obtained in the mother liquor which can be recovered and sold as a fertilizer.

DESCRIPTION OF THE PRIOR ART 4-hydroxyacetophenone oxime is used to prepare N-acetyl-para-aminophenol (APAP) which is a commercially significant and important analgesic.

A process for the preparation of APAP utilizing the Beckmann rearrangement of the 4-HAP oxime is disclosed and claimed in U.S. Pat. No. 4,524,217, the entire disclosure of which is incorporated by reference.

One key step in the production of APAP, as set forth in said U.S. Pat. No. 4,524,217, involves the preparation of 4-HAP oxime by reacting the same with hydroxylamine salt, e.g., hydroxylamine sulfate, and caustic to form the ketoxime of the ketone and then subjecting said 4-HAP ketoxime to a Beckmann rearrangement in the presence of the catalyst to form APAP.

As pointed out at col. 4 of said U.S. Pat. No.4,524,217, the conversion of 4-HAP oxime is accomplished by contacting the same with a hydroxylamine salt such as hydroxlamine hydrochloride, hydroxylamine sulfate (HAS), hydroxylamine bisulfate or hydroxylamine phosphate in a base such as ammonium hydroxide, potassium hydroxide, sodium hydroxide, lithium hydroxide. As pointed out at line 53 in said col. 4, 1-3 mols of base per mol of hydroxylamine is utilized in order to get acceptable reaction rates and yields. Since hydroxylamine is sensitive and decomposes in its free form, it is shipped as a salt, e.g., hydroxylammonium sulfate. The free hydroxylamine is liberated upon treatment of the salt with a base, such as ammonium hydroxide or sodium hydroxide.

A study of the oximation reaction shows that a rate maximum is achieved at a pH of about 4-5. The rate of reaction decreases as the pH is either raised or lowered. The addition of the base to aqueous hydroxylammonium sulfate produces via a buffering effect a pH near this optimum. As previously indicated, this reaction is well known in the art.

In a proposed commercial operation for the manufacture of APAP according to the Beckmann rearrangement of the corresponding ketoxime, it has been ascertained that in a single pass operation regarding the production of 4-HAP oxime from 4-HAP by treating the same with HAS and caustic, a mother liquor is obtained wherein the concentration of the ammonium sulfate is about 8 wt. %. As can well be appreciated, this dilute solution adds an economic penalty to the overall efficiency of the process in that it is uneconomical to sell the dilute solution since the cost of extracting the ammonium sulfate would be too high. The other alternative is to dispose of the same and, as can well be appreciated, this causes all sorts of economic as well as environmental problems.

SUMMARY OF THE INVENTION

It has now been found that part of the mother liquor can be recycled back to the ketoxime production vessel without suffering color problems providing certain critical ratios of reactants are utilized. The amount of caustic which is used must be slightly more than the amount of 4-HAP which is to be reacted. On a molar basis, 1-4% excess base with regard to 4-HAP is utilized. On the other hand, the amount of base must be slightly less than the free hydroxylamine. On a molar basis, 1-4% more free hydroxylamine is used than base. As has been previously mentioned, free hydroxylamine is sensitive and is sold commercially as a salt. One mol of hydroxylammonium sulfate (HAS) yields 2 moles of free amine when treated with caustic in accordance with the following reaction:

(NH$_3$OH)$_2$
SO$_4$+2NaOH→2NH$_2$OH+Na$_2$SO$_4$+2H$_2$O

Thus, when using a hydroxylamine salt such as HAS, as a source of hydroxylamine, ½mol of HAS=1 mol of free hydroxylamine.

If the typical excess base is used, color bodies form as a result of reactions with 4-HAP and these color bodies can affect the color of the desired APAP.

It was indeed unexpected that operating with a small amount of base would have a beneficial effect in view of the teachings of the prior art that excess base was required. The novel process of this invention is carried out in a relatively simple manner.

4-HAP oxime is produced from 4-HAP by reaction of the same with a hydroxylamine salt and excess base as is conventional in the prior art and the desired product, the 4-HAP oxime, is crystallized from the mother liquor and the mother liquor is then recycled back to use as a starting material for the production of additional 4-HAP oxime. It is noted that only about 50% of the mother liquor can be recycled back if the usual 30% hydroxylamine sulfate (HAS) solution is used for oxime production. This is because the remainder of the water, i.e., the reaction solvent, is supplied by the water in the HAS solution. Conditions utilized with regard to temperature and pressure are those conventional in the prior art and include temperatures of from 0°-100° C. for periods of time of 1-4 hours. Any pressure can be used, e.g., 80 mm of mercury to 10 atmosphere absolute.

A preferred embodiment of this invention resides in the use of HAS and ammonium hydroxide as the base. Calculations have shown that in a typical one pass operation (no recycle), the concentration of ammonium sulfate in the mother liquor is about 8%. The recycle process of this invention can increase the ammonium sulfate concentration to about 15 Wt.%. Quite obviously, ammonium sulfate is a known fertilizer and the more concentrated solution can be sold or said salt can be recovered.

The following examples will now illustrate the best mode contemplated for carrying out the invention. In the examples which follow, the recycle operation of this invention is set forth utilizing both ammonium hydroxide and sodium hydroxide. Additionally, a comparative example is presented wherein a recycle operation was attempted using caustic outside the ranges of this invention. As will be seen from the example, the use of the conventional amount of caustic resulted in off-color product.

It is noted that the concentration of sulfate ion was theoretically calculated and it was determined that in a recycle operation, the amount of sulfate ion stabilizes somewhere between the third and fourth recycle.

In order to expedite the experiments which follow, sulfate was deliberately added in order that the experiments would simulate beginning from the third or fourth recycle.

EXAMPLE 1

4-HAP oxime prepared with recycles using a 2.6% molar excess of caustic to 4-hydroxyacetophenone and a 1.6% molar deficiency of caustic to hydroxylamine.
1. A 1-L round bottom flask was charged with 4-HAP (100 g, 0.74 mol), sodium sulfate (46 g), 29% hydroxylammonium sulfate solution (186 mL, 0.39 mol), water (260 mL).
2. The contents of the flask were heated and stirred until all the solids dissolved (ca. 80° C.).
3. 50% NaOH (40 mL, 0.76 mol) and water (50 mL) were placed in an addition funnel. The caustic was added dropwise over a 15 minute period.
4. The contents were refluxed for 30 minutes and then allowed to crystallize slowly with stirring to 20° C.
5. The crystals were filtered and washed with 100 mL of ice water.
6. The combined mother liquors were saved for recycle and the solids dried on a rotatory evaporator at 60° C.
7. A 1-L round bottom flask was charged with 4-HAP (100 g, 0.74 mol), 29% hydroxylammonium sulfate solution (186 mL, 0.39 mol), and 260 mL of mother liquor from the previous run.
8. The contents of the flask were heated and stirred until all the solids dissolved (ca. 80° C.).
9. 50% NaOH (40 mL, 0.76 mol) and water (50 mL) were placed in an addition funnel. The caustic was added dropwise over a 15 minute period.
10. The contents were refluxed for 30 minutes and then allowed to crystallize slowly with stirring to 20° C.
11. The crystals were filtered and washed with 100 mL of ice water.
12. The combined mother liquors were saved for recycle and the solids dried on a rotatory evaporator at 60° C. This recycle scheme was repeated for a total of 5 cycles. The weight of the recovered 4-HAP oxime on the fifth cycle was 105.7 g. The 4-HAP oxime product was a white crystalline material and the mother liquor was straw yellow in appearance.

EXAMPLE 2

4-HAP oxime prepared with recycles using a 2.6% molar excess of caustic to 4-hydroxyacetophenone and a 1.3% molar deficiency of caustic to hydroxylamine.
1. A 1-L round bottom flask was charged with 4-HAP (100 g, 0.74 mol), ammonium sulfate (46 g), 29% hydroxylammonium sulfate solution (186 mL, 0.39 mol), water (290 mL).
2. The contents of the flask were heated and stirred until all the solids dissolved (ca. 80° C.).
3. Concentrated ammonium hydroxide (52 mL, 0.77 mol) was placed in an addition funnel. The base was added dropwise over a 10 minute period.
4. The contents were refluxed for 30 minutes and then allowed to crystallize slowly with stirring to 20° C.
5. The crystals were filtered and washed with 100 mL of ice water.
6. The combined mother liquors were saved for recycle and the solids dried on a rotatory evaporator at 60° C.
7. A 1-L round bottom flask was charged with 4-HAP (100 g, 0.74 mol), 29% hydroxylammonium sulfate solution (186 mL, 0.39 mol), and 290 mL of mother liquor from the previous run.
8. The contents of the flask were heated and stirred until all the solids dissolved (ca. 80° C.).
9. Concentrated ammonium hydroxide (52 mL, 0.77 mol) was placed in an addition funnel. The base was added dropwise over a 10 minute period.
10. The contents were refluxed for 30 minutes and then allowed to crystallize slowly with stirring to 20° C.
11. The crystals were filtered and washed with 100 mL of ice water.
12. The combined mother liquors were saved for recycle and the solids dried on a rotatory evaporator at 60° C. This recycle scheme was repeated for a total of 5 cycles. The weight of the recovered 4-HAP oxime on the fifth cycle was 109.5 g. The 4-HAP oxime product was an off-white crystalline material and the mother liquor was straw yellow in appearance.

EXAMPLE 3

4-HAP oxime prepared with recycles using a 20% molar excess of caustic to 4-hydroxyacetophenone and a 14% molar excess of caustic to hydroxylamine.
1. A 1-L round bottom flask was charged with 4-HAP (100 g, 0.74 mol), sodium sulfate (46 g), 29% hydroxylammonium sulfate solution (186 mL, 0.39 mol), water (260 mL).
2. The contents of the flask were heated and stirred until all the solids dissolved (ca. 80° C.).
3. 50% NaOH (47 mL, 0.89 mol) and water (50 mL) were placed in an addition funnel. The caustic was added dropwise over a 15 minute period.
4. The contents were refluxed for 30 minutes and then allowed to crystallize slowly with stirring to 20° C.
5. The crystals were filtered and washed with 100 mL of ice water.
6. The combined mother liquors were saved for recycle and the solids dried on a rotatory evaporator at 60° C.
7. A 1-L round bottom flask was charged with 4-HAP (100 g, 0.74 mol), 29% hydroxylammonium sulfate solution (186 mL, 0.39 mol), and 260 mL of mother liquor from the previous run.
8. The contents of the flask were heated and stirred until all the solids dissolved (ca. 80° C.).
9. 50% NaOH (47 mL, 0.89 mol) and water (50 mL) were placed in an addition funnel. The caustic was added dropwise over a 15 minute period.
10. The contents were refluxed for 30 minutes and then allowed to crystallize slowly with stirring to 20° C.

11. The crystals were filtered and washed with 100 mL of ice water.
12. The combined mother liquors were saved for recycle and the solids dried on a rotatory evaporator at 60° C. This recycle scheme was repeated for a total of 5 cycles. The weight of the recovered 4-HAP oxime on the fifth cycle was 102.6 g. The 4-HAP oxime product was a dark gray crystalline material and the mother liquor was dark orange in appearance.

| Analysis of final mother liquor for above runs | | | |
| --- | --- | --- | --- |
|  | Example 1 | Example 2 | Example 3 |
| % 4-HAP | 0.41 | 0.36 | 0.17 |
| % Oxime | 0.31 | 1.2 | 1.1 |
| % APAP | 0.13 | ND | ND |
| % Unknowns | ND | ND | 0.01 |
| % Sulfate | 8.34 | 15.7 | — |
| % Carbon | 0.7 | 1.0 | — |
| % Hydrogen | 11.6 | 9.7 | — |
| % Nitrogen | 0.5 | 5.1 | — |

Note: The sulfate numbers are not believed to be very accurate.

The above examples clearly illustrate that operation within the critical parameters of this invention resulted in the production of 4-HAP oxime having acceptable color.

Comparative Example 3 using excess base resulted in an off-color product which was not acceptable and/or less desirable in the preparation of pharmaceutical compositions.

Please note that in the analysis of the final mother liquor, the analytical procedures were not very reliable so that the exact numbers in connection with the % sulfate are subject to question. Nevertheless, the trend is accurate, i.e., the recycle operation of this invention resulted in a definite increase in ammonium sulfate in the mother liquor.

What is claimed is:
1. In the process for the production of 4-hydroxyacetophenone oxime by the conversion of 4-hydroxyacetophenone utilizing hydroxylamine, the improvement which comprises forming said 4-hydroxyacetophenone oxime and crystallizing the same from a mother liquor; washing said crystallized 4-acetophenone oxime; combining said wash water with said mother liquor; and recycling at least a portion of said combined liquor back to the reaction vessel for oxime production while maintaining the following mol ratio of reactants:
   caustic:4-hydroxyacetophenone 1-4% molar excess
   caustic:hydroxylamine 1-4% molar deficiency.
2. The process of claim 1 wherein said source of hydroxylamine is hydroxylammonium sulfate and said base is ammonium hydroxide.
3. The process of claim 2 wherein the total amount of mother liquor recycled is about 50 wt. %
4. The process of claim 2 wherein a waste stream is recovered containing about 15 wt. % of ammonium sulfate.

* * * * *